United States Patent [19]

Fukukita et al.

[11] Patent Number: 4,754,760
[45] Date of Patent: Jul. 5, 1988

[54] ULTRASONIC PULSE TEMPERATURE DETERMINATION METHOD AND APPARATUS

[75] Inventors: Hiroshi Fukukita, Tokyo; Shinichirou Ueno, Machida, both of Japan

[73] Assignees: Agency of Industrial Science & Technology; Ministry of International Trade & Industry, both of Tokyo, Japan

[21] Appl. No.: 31,372

[22] Filed: Mar. 30, 1987

[30] Foreign Application Priority Data

Nov. 13, 1986 [JP] Japan ................. 61-268662

[51] Int. Cl.$^4$ ................. A61B 10/00; G01N 29/00
[52] U.S. Cl. ................. 128/660; 128/736; 73/599; 374/117
[58] Field of Search ................. 728/660–663; 73/597, 599–600, 602; 374/117–119

[56] References Cited

U.S. PATENT DOCUMENTS

| | | | |
|---|---|---|---|
| 4,246,784 | 1/1981 | Bowen | 128/736 X |
| 4,513,749 | 4/1985 | Kino et al. | 128/660 |
| 4,513,750 | 4/1985 | Heyman et al. | 128/736 X |
| 4,566,460 | 1/1986 | Sato et al. | 128/660 |
| 4,594,896 | 6/1986 | Cardoso et al. | 73/599 |
| 4,607,341 | 8/1986 | Monchalin | 73/602 X |
| 4,610,255 | 9/1986 | Shimura et al. | 128/660 |
| 4,664,123 | 5/1987 | Iinuma | 128/660 |
| 4,679,565 | 7/1987 | Sasaki | 128/660 |
| 4,700,571 | 10/1987 | Okazaki | 128/660 X |

OTHER PUBLICATIONS

Sachs, T. D. et al "TAST: A Non-Invasive Tissue Analytic System", NBS Publ. 453, Proc. of Seminar on Ultrasonic Tissue characterization held at NBS, Gaithersburg, MD, May 28–30, 1975 (issued Oct. 1976).

Primary Examiner—Francis J. Jaworski
Attorney, Agent, or Firm—Oblon, Fisher, Spivak, McClelland & Maier

[57] ABSTRACT

A first ultrasonic pulse formed by the superposition of a probe pulse on a pump pulse having a frequency lower than the center frequency of the ultrasonic probe pulse where the particle velocity of the pump pulse is in the vicinity of zero in addition to which the particle acceleration of which is at a constant portion, and a second pulse formed by the superposition of the probe pulse center frequency on the peak particle velocity portion of the pump pulse, as well as a probe pulse alone, are transmitted into a specimen before and after it is heated and the reflections of the transmitted signals from two or more reflecting points that are at different depths in the specimen are received. The received signals are subjected to frequency analysis and the spectral shift and the phase shift of the probe pulse and superposed pulses are obtained, and from these values the attenuation of the probe pulse between the differing depths is determined. Such an attenuation determination is obtained before and after heating of the specimen and the change in temperature of the specimen is determined from the obtained attenuation values on the basis of a pre-prepared table of changes in attenuation factor in accordance with changes in the temperature of the specimen.

8 Claims, 4 Drawing Sheets

ULTRASONIC PULSE TEMPERATURE DETERMINATION METHOD AND APPARATUS

FIELD OF THE INVENTION AND RELATED ART STATEMENT

The present invention relates to ultrasonic attenuation characteristic and a temperature measuring method and apparatus that utilizes ultrasonic waves to determine temperature changes inside a living body by utilizing the temperature dependency of the acoustic characteristics of tissues in the body obtained by, for example, receiving reflected ultrasound waves that have been transmitted into the body.

Ultrasonic diagnostic devices are known which perform measurements inside a living organism by means of ultrasonic waves. Most of these ultrasonic diagnostic devices employ the pulse reflection method whereby the measurements are performed by transmitting ultrasonic pulses into a living organism and using information obtained from the pulses reflected back from tissues in the organism. With the pulse reflection method, information from the organism is collected to display a two-dimensional tomographic image of the organism by utilizing the intensities of the reflections echoing back from tissue interfaces within the organism that have different acoustic impedances, which is to say amplitude values, and the propagation times of the ultrasonic pulses. However, in recent years, with respect to ultrasonic diagnostic devices for mainly determination of the shape of in vivo organisms, there has been a rising demand for ultrasonic diagnostic devices by means of which information can be obtained other than that of the shape of tissues. One example of such information is the internal temperature of an organism. If information on the internal temperature of the in vivo organisms could be obtained, it would be possible to monitor temperature levels in the heat treatment of cancer. It is possible to determine internal temperature changes in vivo by, for example, measuring the degree of attenuation of the ultrasonic pulses and sonic velocity temperature differentials, and then comparing these with previously examined coefficients of temperature dependence of ultrasonic attenuation and sonic velocities of in vivo internal tissues. With, however, most living tissues being comprised of non-homogeneous scattering bodies, obtaining such attenuation or sonic velocity information about the tissues is not easy. For example, when the ultrasonic pulse reflection method is used to find the ultrasonic attenuation in a living organism, the ultrasound reflections are frequency-analyzed, but because the ultrasonic scattering properties of the living organism included in the analysis results have an extremely large frequency dependency characteristic, it is difficult to obtain with accuracy the acoustic attenuation characteristics from the analysis results. As methods of reducing the effect of these scattering characteristics, there is known, for example, the arrangement described in Proceedings of the IEEE, Vol. 73, No. 7, 1985, pages 1159 to 1168. Hereinbelow will be described the prior art attenuation characteristics determination method, with reference to FIG. 1.

In FIG. 1, the numeral 1 denotes a specimen that is the object of examination; 2 is an ultrasonic probe for transmitting/receiving ultrasonic pulses to/from the specimen 1; 3 is a pulse driver for driving the ultrasonic probe 2; 4 is an amplifier for amplifying the signals received from the ultrasonic probe 2; 5 is an A/D converter for converting the digital signals output from the amplifier 4; and 6 is a CPU for performing processing such as frequency analysis of the output from the A/D converter 5.

The operation of the above arrangement will now be described hereinbelow.

First, a driving pulse is transmitted from the pulse driver 3 to the ultrasonic probe 2, and the ultrasonic probe 2 generates an ultrasonic pulse. The ultrasonic pulse thus generated is propagated within the specimen 1 and is scattered by discontinuities in the acoustic properties of the encountered tissues, and one part thereof is thereby returned along the propagation path, that is, along the line of acoustic scanning, back to the ultrasonic probe 2, and is converted into a received signal. In this propagation and scattering process the ultrasonic pulse is influenced by the ultrasonic wave attenuation and scattering characteristics of the tissue. The received signal is amplified by the amplifier, converted by the A/D converter 5 into a digital signal, undergoes signal processing such as frequency analysis and the like by the CPU 6, and the attenuation characteristics are calculated. The attenuation characteristics are calculated as follows. First, a received signal h(a) corresponding to a specific depth a in the specimen 1 and a received signal h(b) corresponding a depth b are extracted. The length of the extracted signal inside the specimen 1, for example, 1 cm, calculated in terms of a timebase is in the order of 13 $\mu$s. Next, h(a) and h(b) are subjected to frequency analysis, for example, Fourier transformation, to obtain respective frequency characteristics H(a, $\omega$) and H(b, $\omega$). Here $\omega$ is angular frequency. H(a, $\omega$) and H(b, $\omega$) can be represented as follows.

$$H(a, \omega) = T(\omega)\, G(a, \omega)\, S(a, \omega) \tag{1}$$

$$H(b, \omega) = T(\omega)\, G(b, \omega)\, S(b, \omega) \tag{2}$$

Here, $T(\omega)$ is the frequency characteristic of the ultrasonic pulses generated by the ultrasonic probe 2; $G(a, \omega)$ is the ultrasonic propagation characteristic received between the ultrasonic probe 2 and the depth a in the specimen 1; and $S(a, \omega)$ is the ultrasonic wave scattering characteristic at the depth a. If scattering characteristics $S(a, \omega)$ and $S(b, \omega)$ are equal, they are cancelled out by equations (1) and (2), and by obtaining absolute values as shown by the following equation, the attenuation $E(b, a, \omega)$ of the ultrasonic pulse between depth a and depth b in the specimen 1 can be obtained.

$$\begin{aligned} E(b, a, \omega) &= G(b, \omega)/G(a, \omega) \\ &= H(b, \omega)/H(a, \omega) \end{aligned} \tag{3}$$

It is thus possible to obtain the attenuation characteristic at any desired region within the specimen 1. However, generally speaking, the ultrasonic wave scattering characteristics inside an organism differ greatly depending on the region, and it is not possible to assume as in the above that $S(a, \omega)$ and $S(b, \omega)$ are equal.

Because of this, reverse utilization is made of the fact that the ultrasonic scattering characteristics change randomly according to the region. That is, if with respect to the specimen 1 the position at which the ultrasonic probe 2 transmits and receives the ultrasonic pulses is moved transversely within a specified range in many and frequency analysis is performed on the received signals thus obtained from a number of regions, and the many frequency analysis results are averaged, just the randomly varying ultrasonic wave scattering characterisrics S(a, ω) and S(b, ω) are cancelled out. It thus becomes possible to apply the equation (3) to the Fourier transformations H(a, ω) and H(b, ω) thus obtained, and find the attenuation characteristics.

However, in the aforesaid type of arrangement, when the regions of determination of the ultrasonic pulse scattering characteristics in the specimen 1 shift, the premise has to be that the changes are perfectly random; that is, that there is no correlation between the different determination regions. However, there has been a problem that this premise does not hold in a living organism that usually has structures possessing clear acoustic boundaries.

OBJECT AND SUMMARY OF THE INVENTION

The purpose of this invention is to provide a method and device for determining accurately the ultrasonic attenuation characteristics and temperature changes in a desired specimen having ultrasonic scattering characteristics, for example, a living organism.

In order to achieve the aforesaid object, the method and device according to this invention comprise a method and device for determining temperature in which an ultrasonic pulse formed by the superposition of the probe pulse on a pump pulse having a frequency lower than the center frequency of the ultrasonic probe pulse where the particle velocity of the pump pulse is in the vicinity of zero in addition to which the particle acceleration of which is at a constant portion, and a pulse formed by the superposition of the probe pulse center frequency on the peak particle velocity portion of the pump pulse are transmitted into the specimen before and after heating thereof, the reflections of the transmitted signals from two or more reflecting points that are at different depths in the specimen are received, the received signals are subjected to frequency analysis and the spectral shift and the phase shift of the probe pulse are obtained, and from these values the attenuation of the probe pulse between the differing depths in the specimen before and after heating is obtained and the change in temperature of the specimen is determined from the obtained attenuation values on the basis of pre-prepared table of changes in attenuation factor in accordance with changes in the temperature of the specimen.

In this invention, the ultrasonic probe pulse is superposed on a pump pulse having a frequency lower than the center frequency of the probe pulse where the particle velocity of the pump pulse is in the vicinity of zero and in addition at a portion where the particle acceleration of the pump pulse is constant. More specifically, the centroid of the ultrasonic probe pulse is superposed when the particle velocity of the pump pulse is in the vicinity of zero, and the value thereof changes from negative to positive (hereinafter referred to as phase state C), i.e., when the particle acceleration is positive; or when the particle velocity of the pump pulse is in the vicinity of zero and the value thereof changes from positive to negative, i.e., when the particle acceleration is negative (hereinafter referred to as phase state D).

Thus, two pulses obtained by superposing the probe pulse center frequency on the pump pulse phase state C and phase state D are transmitted together with the probe pulse into the specimen before and after the heating thereof, and the reflections of the transmitted signal from two or more reflecting points that are at different depths in the specimen are received, the received signal is subjected to frequency analysis and the spectral shift and the phase shift of the probe pulse are obtained, and from these values the attenuation of the probe pulse between the differing depths in the specimen before and after heating is obtained and the change in temperature of the specimen is determined from the obtained attenuation values on the basis of a pre-prepared table of changes in attenuation factor in accordance with changes in the temperature of the specimen.

Therefore, with this invention, information on the internal temperature of the living organism can be obtained, making it possible to utilize it for temperature monitoring in heat treatment of cancer and the like.

The temperature determining apparatus according to this invention comprises at least a probe wave transducer which sends out ultrasonic pulses and a phase control driver means for a pump wave transducer which transmits ultrasonic pulses of a lower frequency than the ultrasonic pulses of the probe wave transducer, means of detecting the amount of the spectral shift and the amount of the phase shift in the signal received by the probe wave transducer, and means of computing temperature change from the amount of spectral shift and the amount of phase shift.

Other objects and features of the invention will become clear from the following explanation made with reference to the accompanying drawings.

DETAILED DESCRIPTION OF THE PREFERRED EMBODIMENTS

Figure 1:
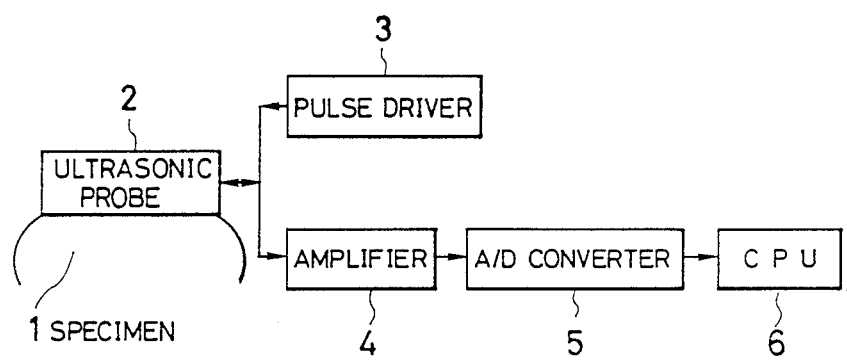
FIG. 1 is a functional block diagram showing ultrasonic attenuation determination according to the prior art.
Figure 2:
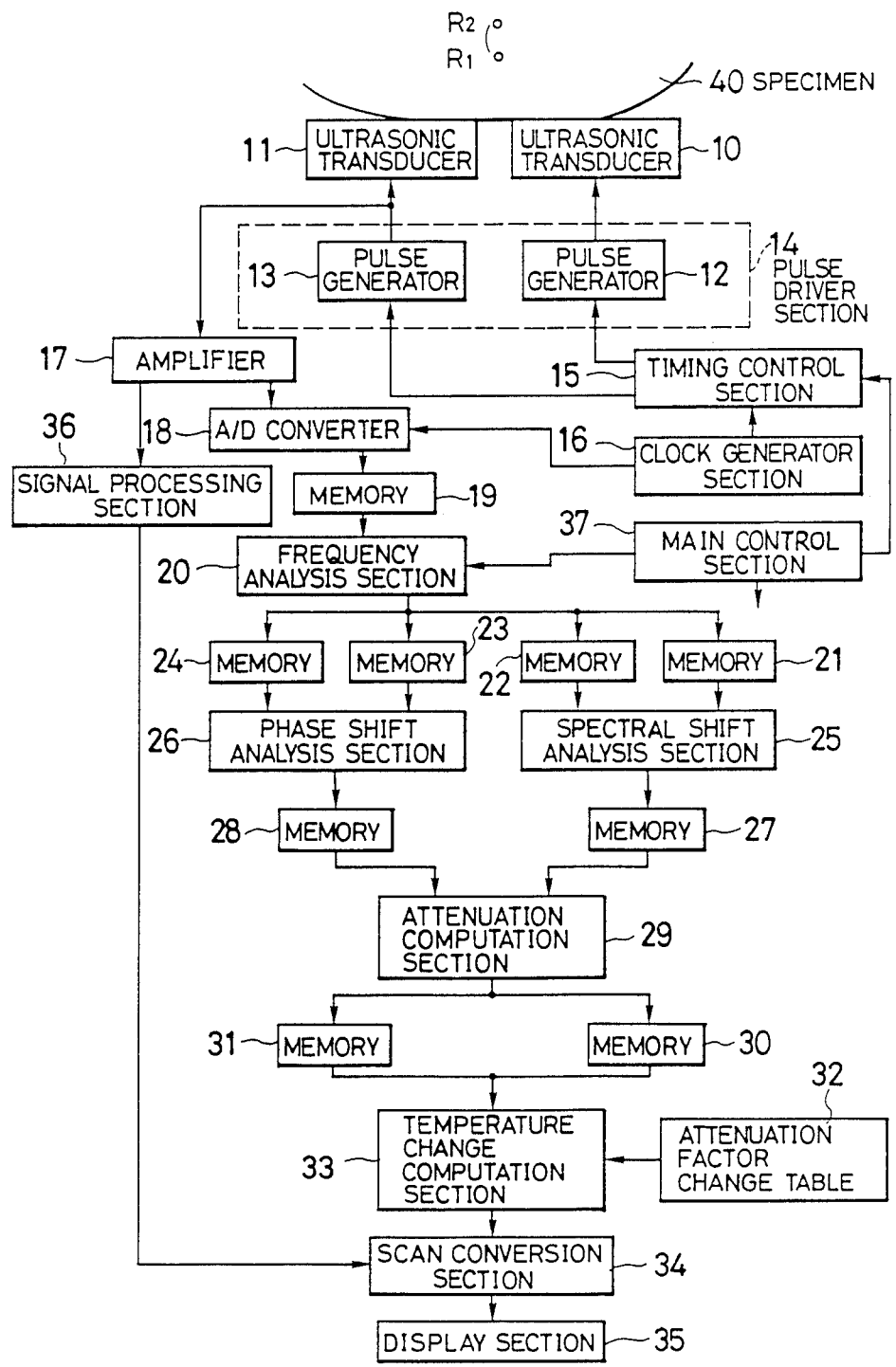
FIG. 2 is a functional block diagram of an embodiment of an ultrasonic temperature determining apparatus according to the present invention

With reference to FIG. 2 which shows a functional block diagram of an embodiment of an ultrasonic temperature determination apparatus according to the present invention, numeral 10 is an ultrasonic transducer for the pump pulses; 11 is an ultrasonic transducer for the probe pulses; 12 is a pulse driver to drive the ultrasonic transducer 10; 13 is a pulse driver to drive the ultrasonic transducer 11; 14 is a pulse driver section comprised of the pulse drivers 12 and 13; 15 is a timing control section for controlling the phasal relationship of the outputs of the pulse drivers 12 and 13; 16 is a clock generator section which supplies clocks to the timing control section 15; 17 is an amplifier for amplifying the received signals coming from the ultrasonic transducer 11; 18 is an A/D converter for converting the output of the amplifier 17 to digital data; 19 is a memory for storing the output of the A/D converter 18; 20 is a frequency analysis section for analysing data that is stored in the memory 19; 21, 22, 23 and 24 are memories for storing the output of the frequency analysis section 20; 25 is a spectral shift analysis section for analyzing the degree of spectral shift from the data stored in memories 21 and 22; 26 is a phase shift analysis section for analyzing the degree of phase shift from the data stored in memories 23 and 24; 27 is a memory for storing the output of the spectral shift analysis section 25; 28 is a memory for storing the output of the phase shift analysis section 26; 29 is an attenuation computation section for obtaining attenuation data from the data stored in the memories 27 and 28; 30 and 31 are memories for storing the output of the attenuation computation section 29; 33 is a temperature change computation section for finding changes in temperature from the memories 30 and 31 and the attenuation factor change table 32; 34 is a scan conversion section for scan conversion of the output of the temperature change computation section 33; 35 is a display section for displaying the output of the scan conversion section 34; 36 is a signal processing section for additive signal processing of the output of the amplifier 17; and the output of the signal processing section is applied to the scan conversion section 34. The numeral 37 denotes a main control section for control of the overall system; 40 is a specimen; and R1 and R2 are ultrasonic scatterers that are within the specimen 40 at a depth of a and b, respectively.

The operation of the above construction will now be explained hereinbelow.

Figure 3A:
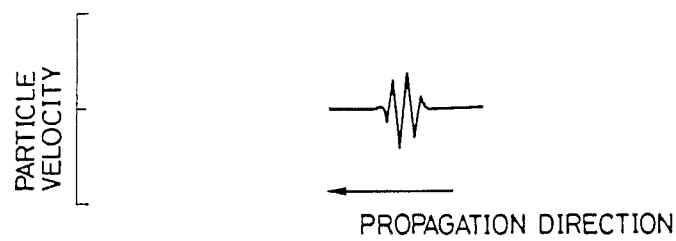
FIGS. 3a to 3d are output waveforms of the ultrasonic transducer of an embodiment of the present invention.
Figure 3B:
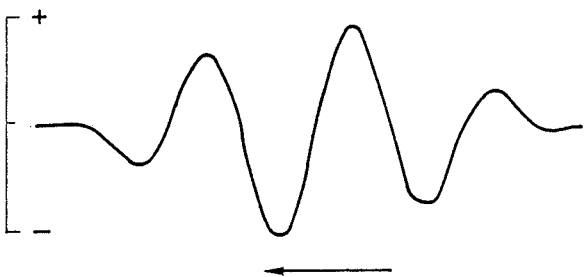
Figure 3C:
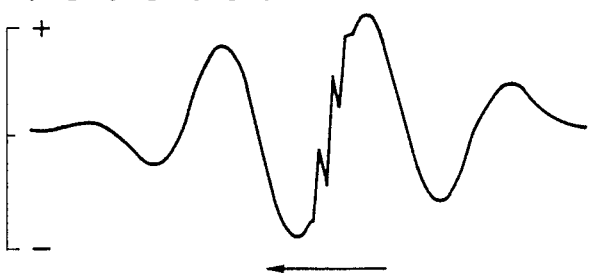
Figure 3D:
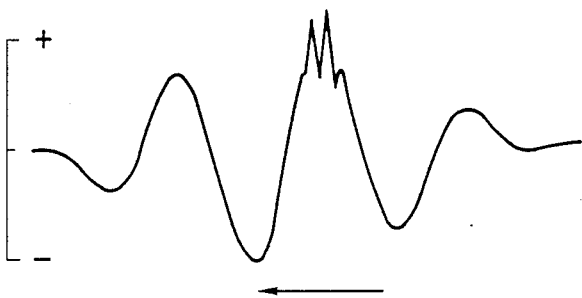

FIG. 3a shows an example of the ultrasonic pulse wave output of the probe ultrasonic transducer 11; FIG. 3b shows an example of the ultrasonic pump wave output of the probe ultrasonic transducer 10; FIG. 3c shows an example of the superposition in the phase state C of the ultrasonic pulse outputs of the probe ultrasonic transducers 10 and 11; and FIG. 3d shows an example of the superposition in the phase state D of the ultrasonic pulse outputs of the probe ultrasonic transducers 10 and 11. The frequency selected for the pumping ultrasonic pulse wave, that is, the pump pulse, is for example 0.4 MHz, and the frequency selected for the probe ultrasonic pulse, that is, the pump pulse, is for example 4.0 MHz, so that the center frequencies thereof differ considerably. In the phase state C, the centroid of the ultrasonic probe pulse is superposed when the particle velocity of the pump pulse is in the vicinity of zero and moreover when the value thereof changes from negative to positive, that is, when the particle acceleration is positive. In the phase state D, the centroid of the probe pulse is superposed when the particle velocity of the pump pulse peaks. Regarding the waveforms of the probe pulse and the pump pulse, if the pump pulse wavelength is taken as $\lambda$ and the length of the probe pulse as W, then preferably:

$$W < \lambda/2$$

This facilitates the analysis of the probe pulse spectral shift and phase shift.

The propagation in the specimen 40 of the probe pulse and the ultrasonic pulses superposed in the phase states C and D will now be explained in detail. Even with the peak ultrasonic output levels that can be used with the usual ultrasonic diagnostic devices, owing to the non-linearity of the propagation the speed $C_1$ at which the ultrasonic pulse propagates differs between the peaks and valleys of the waveform. This relationship can be represented by the following equation.

$$C_1 = C_0 + (1 + \tfrac{1}{2}(B/A))u = C_0 + \Delta C \quad (4)$$

Figure 4A:
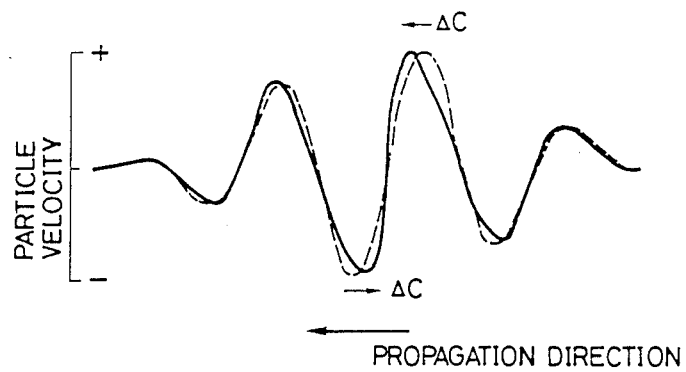
FIGS. 4a to 4c are pulse waveforms showing distortion produced by the non-linear propagation phenomenon.
Figure 4B:
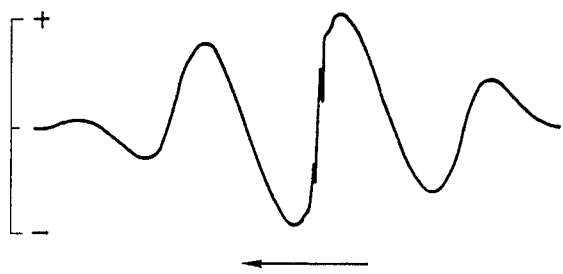
Figure 4C:
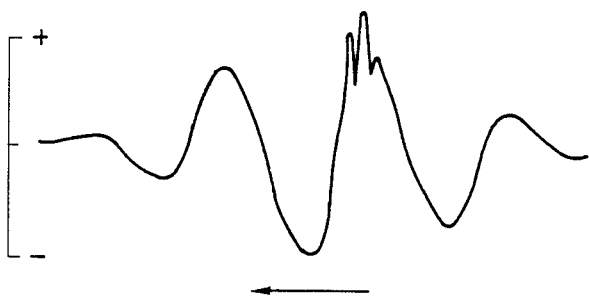

Here, B/A is the non-linear parameter of the propagating medium; although in the case of a living body this varies according to the type of tissue, it is for example a value in the order of 6. $C_0$ is the phase velocity of an ultrasonic pulse of infinitely small amplitude, u is the particle velocity and is a function of instanteous pulse amplitude, and $\Delta C$ is the propagation speed differential. At an ultrasonic pulse power of 1 W/cm$^2$ the particle velocity u in water is 12 cm/sec. In this case, C will be about 50 cm/sec. The non-linearity of the propagation affects the ultrasonic waveform as shown in FIG. 4. FIG. 4a shows the distortion caused by the non-linear propagation of the pump pulse, and FIGS. 4b and 4c show the changes in the probe pulse frequency characteristics caused by the non-linearity of the pump pulse propagation. In FIG. 4b, the center frequency of the probe pulse superimposed in the phase state C shows an upward shift in frequency with the propagation, while in FIG. 4c the phase of the probe pulse superimposed in the phase state D is shifted by the propagation. The phase differential in the probe pulse between when the pump pulse is being superimposed in the phase state D and when it is not, that is, the degree of phase shift, $\Delta P$, can be represented by the following equation.

$$\Delta P = 2 \cdot \Delta x \cdot \omega \cdot 1/C_0 - 1/(C_0 + \Delta C) \quad (5)$$

In the organism, if it is assumed that the phasal velocity $C_0$ becomes 1,500 m/sec, the propagation distance $\Delta x$ is 1 cm and the angular frequency $\omega$ is $2\pi \times 4 \times 10^6$ rad/sec, $\Delta P$ becomes 0.11 rad (=6.4 degrees), enabling detection to be carried out with an adequately good level of precision.

The procedure of processing the signals received from the probe pulse shown in FIG. 3a and the ultrasonic pulse output having the relationship shown in FIGS. 3c and 3d reflected by the reflectors R1 and R2 will now be explained. With the ultrasonic transducer 10 in the non-operating state, a probe pulse generated by the ultrasonic transducer 11 is propagated within the specimen 40 and is scattered by discontinuities in the acoustic properties of the encountered tissues, one part thereof being thereby returned along the propagation path, that is, along the line of acoustic scanning, back to the ultrasonic transducer 11 and is converted into a received signal. During this process, the ultrasonic pulse is influenced by the ultrasonic attenuation and scattering characteristics of the tissues. The received signal is amplified by the amplifier 17 and converted by the A/D converter 18 into digital data. Sampling timing by the A/D converter 18 is phase-synchronized with the pulse driver 13, the sampling rate thereof being several tens of megahertz and the minimum resolution in the order of 10 bits, it being necessary to accurately preserve the phase information of the input signals. The output of the A/D converter 18 is stored in the memory 19. The frequency analysis section 20 extracts the data held in the memory 19 and performs computations such as frequency analysis and the like. Specific examples of computations are amplitude spectrum calculation and phase angle calculation, using computing algorithms such as Fourier integration, DFT (distributed Fourier transforms), and so forth. Amplitude spectrum and phase angle are calculated as follows. First, a received signal h(a) corresponding to a specific depth a in the specimen 40 is taken from the memory 19 and is frequency analyzed and the Fourier transform H(a, $\omega$) obtained, and likewise a received signal h(b) corresponding to a specific depth b is taken from the memory 19 and is frequency analyzed and the Fourier transform H(b, ω) obtained. The length from the extracted data is, for example, 1 cm inside the specimen 40, or converted to time period is in the order of 13 μs. The amplitude spectrum A(a, ω) can be represented as an absolute Fourier transform H(a, ω) value and the phase angle P(a, ω) as a Fourier transform H(a, ω) phase angle by the following equations.

$$A(a, \omega) = |H(a, \omega)| \quad (6)$$

$$P(a, \omega) = arg(H(a, \omega)) \quad (7)$$

The amplitude spectrum A(a, ω) and the phase angle P(a, ω) thus obtained are heavily influenced by the scattering frequency characteristics of the scatterers R1 and R2 in the specimen 40, making it difficult to accurately obtain the ultrasonic attenuation characteristics of the specimen 40. An amplitude spectrum A(a, ω) corresponding to a specific depth a and an amplitude spectrum A(b, ω) corresponding to a specific depth b are stored in the memory 21, and a phase angle P(a, ω) corresponding to a specific depth a and a phase angle P(b, ω) corresponding to a specific depth b are stored in the memory 23.

There now follows an explanation with respect to the superposing of the pump pulse on the probe pulse.

First, in the case of propagation in the specimen 40 with the pump pulse and probe pulse superposed in the phase state C, the propagation can approximated as follows. Regarding the path of the propagation as a collection of minute segments, in these minute segments the superposed ultrasonic pulses will produce propagation distortion on the basis of the non-linearity effect and the center frequency of the probe pulse will undergo an upward shift. The amount of this shift is dependent on both the particle velocity u in the segments in question and the non-linearity parameter B/A of the propagation medium. The probe pulse is thus subjected to excessive attenuation as a result of the upward shift of the center frequency of the probe pulse. This excessive attenuation value is also a function of the attenuation coefficient of the propagation medium. While the above non-linear propagation distortion in the minute segments and the attenuation distortion is sustained while the phase state C is maintained, the ultrasonic pulses propagate and are scattered. Because the amplitude of the ultrasonic pulses on the way back along the propagation path is extremely small, the non-linearity effect can be ignored. The amplitude spectrum Ac (a, ω) of the received signal corresponding to depth a obtained in phase state C and the amplitude spectrum Ac (b, ω) of the received signal corresponding to depth b are stored in memory 22.

In the case of propagation in the specimen 40 with the pump pulse and probe pulse superposed in the phase state D, the probe pulse can be approximated on the basis of just the phase shift it is subjected to as propagation distortion based on the non-linearity effect. Because the amplitude of the ultrasonic pulses on the way back along the propagation path is extremely small, the non-linearity effect can be ignored. The phase angle P(a, ω) of the received signal corresponding to depth a in the specimen obtained in phase state D and the phase angle P(b, ω) of the received signal corresponding to depth b are stored in the memory 24.

Next, the difference between the phase angle obtained with the ultrasonic transducer 10 in the non-operating state and the phase angle obtained in the phase state D, that is, the phase shift amount ΔP, $$\Delta P(a, \omega) = P(a, \omega) - P_D(a, \omega) \quad (8)$$

$$\Delta P(b, \omega) = P(b, \omega) - P_D(b, \omega) \quad (9)$$

and the difference in the phase shift amount at depth b and depth a, i.e., the differential phase shift amount Δφ, $$\Delta\phi = \Delta P(b, \omega) - \Delta P(a, \omega) \quad (10)$$

are calculated by the phase shift analysis section 26 and stored in the memory 28. Also, with equation (10), the ultrasonic scattering characteristics are removed.

Next, the change in the amplitude spectrum obtained with the ultrasonic transducer 10 in the non-operating state and the amplitude spectrum obtained in the phase state C, the spectral shift amount ΔA, $$\Delta A(a, \omega) = AC(a, \omega)/A(a, \omega) \quad (11)$$

$$\Delta A(b, \omega) = AC(b, \omega)/A(b, \omega) \quad (12)$$

and the change in the spectral shift amount at depth b and depth a the differential spectral shift amount Δα, $$\Delta\alpha = \Delta A(b, \omega)/\Delta A(a, \omega) \quad (13)$$

are calculated by the spectral shift analysis section 25 and stored in the memory 27. Also, from equation (1), the spectral shift amount ΔA(a, ω), using propagation characteristics G'(a, ω) in the phase state C, can be represented by $$\Delta A(a, \omega) = |G'(a, \omega)| \quad (14)$$

Therefore, the differential spectral shift amount can be represented as follows as a change in the spectral shift amount, using the ultrasonic attenuation E(b, a, ω) between depth a and depth b and the attenuation E'(b, a, ω) in phase state C.

$$\Delta\alpha = |G'(b, \omega)/G(b, \omega)|/|G'(a, \omega)/G(a, \omega)| \quad (15)$$
$$= E'(b, a, \omega)/E(b, a, \omega)$$

That is, in the Δα obtained by the above equation (13), the ultrasonic scattering characteristics are erased.

From the thus obtained differential phase shift amount Δφ and the differential spectral shift amount Δα, the ultrasonic attenuation E can be found as follows.

The differential spectral shift amount Δα is a quantity that is decided by the ultrasonic attenuation between depth a and depth b, and the pump pulse particle velocity u and the non-linearity parameter B/A of the propagation medium.

The product of the particle velocity u and the non-linearity parameter B/A is found from the differential phase shift amount Δφ. Therefore, the differential spectral shift amount Δα can be established from ultrasonic attenuation E and the differential phase shift amount Δφ. Ultrasonic attenuation E can also be established the other way, from spectral shift amount Δα and differential phase shift amount Δφ. From the spectral shift amount value Δα stored in the memory 27 and the phase shift amount Δφ value stored in the memory 28, the attenuation calculation section 29 establishes the corresponding ultrasonic attenuation value E on the basis of the reference table prepared beforehand. The ultrasonic attenuation value E is stored in the memory 30. The value of the attenuation E(T) for when the specimen is heated is stored in the memory 31. The attenuation factor change table 32 is provided with the ordinary ultrasonic attenuation value E and the ultrasonic attenuation factors E(T) for the various heat levels. The temperature change computation section 33 calculates temperature changes on the basis of the attenuation factor change table 32, from the attenuation values stored in memories 30 and 31. Temperature changes obtained from temperature change computation section 33 are stored at scan conversion section 34 and displayed on the display section 35. The output of the signal processing section 36, which performs logarithmic amplification and envelope detection on the output of the amplifier 17, is connected to the scan conversion section 34 to enable a tomographic image to be formed. The above pulse driver section state control, commands to write to and read from memory, and the various computations and the like are controlled by the main control section 37.

As is clear from the above explanation, in accordance with this embodiment of the present invention, the states of the pulse driver sections are altered and signals are received from different depths within the specimen 40, from which the differential phase shift amount and the differential spectral shift amount are obtained, and from these it is possible to obtain the ultrasonic attenuation and from an attenuation factor change table find changes in temperature occurring inside the specimen.

Thus, as has been seen from the above, this invention enables, with respect to the probe pulse, the spectral shift amount and the phase shift amount with respect to different depths in the specimen of a received signal in the case of the superposition of a pump pulse to be obtained, and the ultrasonic attenuation at the differing depths to be obtained from the differential spectral shift amounts and the differential phase shift amounts which are the changes in these values between the different depths, and temperature changes in the specimen to be obtained on the basis of a table of temperature-dependent changes in attenuation factor, thereby enabling accurate information on temperature changes to be obtained even when the received signals are affected by the complex frequency characteristics of scatterers within the specimen. Therefore, with this invention, internal temperature changes, such as of a living organism, can be obtained, making it possible to utilze it for temperature monitoring in heat treatment of cancer and the like.

What is claimed is:

1. A method for determining temperature of a specimen which utilizes ultrasonic pulses, comprising the steps of: providing an ultrasonic probe pulse having a center frequency, forming a first pulse by superposing the probe pulse on a pump pulse having a a frequency lower than the center frequency of the ultrasonic probe pulse where a particle velocity of the pump pulse is in the vicinity of zero in addition to which a particle acceleration of which is at a constant portion, forming a second pulse by superposing the probe pulse center frequency on a peak particle velocity portion of the pump pulse, transmitting said first and second and probe pulses into the specimen, receiving the reflections of the transmitted signals from two or more reflecting points that are at different depths in the specimen, heating said specimen, repeating said transmitting and receiving steps, subjecting the received signals to frequency analysis and obtaining a spectral shift and a phase shift of the probe pulse and the superposed pulses, and from these values obtaining the attenuation of the probe pulse between differing depths in the specimen before and after heating, and estimating the change in temperature of the specimen from the obtained attenuation values on the basis of a pre-prepared table of changes in attenuation factor in accordance with changes in the temperature of the specimen.

2. The method according to claim 1, wherein said specimen is a living organism.

3. The method according to claim 1 wherein said heating step is a heat treatment of cancer in said specimen.

4. An ultrasonic apparatus for determining the temperature within a region, comprising:
    (a) transudcer means for emitting ultrasonic probe pulses and pump pulses into said region,
    (b) phase control driving means for controlling said transducer means to emit a first pulse comprising a probe pulse having a center frequency superimposed on a pump pulse having a frequency lower than the center frequency of the ultrasonic probe pulse at a first superposition location on said pump pulse, and to emit a second pulse comprising a probe pulse superimpsed on a said pump pulse at a second different location on said pump pulse, and to emit a probe pulse into said region,
    (c) means for receiving said first and second and probe pulse and for detecting the amount of phase shift of the received first and second pulses with respect to said probe pulse,
    (d) means responsive to said receiving means for determining the temperature change within said region from the detected amounts of spectral and phase shifts of said received pulses.

5. An apparatus according to claim 4, wherein said phase control driving means and receiving means include means for controlling the emission and receiving of pulses at successive times, and said temperature determining means determines change in temperature between said successive times.

6. An apparatus according to claim 4 wherein said specimen is a living organism and said temperature change is the temperature change within said region during cancer diathermy treatment, 7. An apparatus according to claim 4 wherein said temperature change determining means comprises means for determining the attenuation within said region from said detected spectral and phase shift amounts and providing an output thereof, and means for determining the temperature change within said region responsive to said attenuation output.

8. An ultrasonic apparatus for determining the attenuation of a region of a specimen, comprising:
    (a) transducer means for emitting ultrasonic probe pulses and pump pulses into said region,
    (b) phase control driving means for controlling said transducer means to emit a first pulse comprising a probe pulse having a center frequency superimposed on a pump pulse having a frequeny lower than the center frequency of the ultrasonic probe pulse at a first superposition location on said pump pulse, and to emit a second pulse comprising a probe pulse superimposed on a said pump pulse at a second different location on said pump pulse, and to emit a probe pulse into said region, (c) means for receiving said first and second and probe pulses and for providing an output indicative of the spectral content thereof, (d) means responsive to said receiving means and spectral content output thereof for determining the amounts of phase shift and spectral shift of the spectral content outputs associated with said first and second pulses with respsect to the spectral content output associated with said probe pulse, and for providing outputs indicative thereof, (e) means for determining the attenuation of said specimen region responsive to said outputs of said phase shift and spectral shift determining means.

* * * * *